(12) United States Patent
Bec et al.

(10) Patent No.: US 12,357,163 B2
(45) Date of Patent: Jul. 15, 2025

(54) CATHETER MOTOR DRIVE UNIT THAT FACILITATES COMBINED OPTICAL COHERENCE TOMOGRAPHY AND FLUORESCENCE-LIFETIME IMAGING

(71) Applicant: The Regents of the University of California, Oakland, CA (US)

(72) Inventors: Julien Bec, Davis, CA (US); Laura Marcu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 339 days.

(21) Appl. No.: 17/923,711

(22) PCT Filed: Mar. 16, 2021

(86) PCT No.: PCT/US2021/022620
§ 371 (c)(1),
(2) Date: Nov. 7, 2022

(87) PCT Pub. No.: WO2021/230978
PCT Pub. Date: Nov. 18, 2021

(65) Prior Publication Data
US 2023/0172443 A1 Jun. 8, 2023

Related U.S. Application Data

(63) Continuation-in-part of application No. 16/500,374, filed as application No. PCT/US2018/027372 on Apr. 12, 2018, now Pat. No. 11,490,818.
(Continued)

(51) Int. Cl.
*A61B 1/04* (2006.01)
*A61B 5/00* (2006.01)
*A61B 5/06* (2006.01)

(52) U.S. Cl.
CPC .............. *A61B 1/043* (2013.01); *A61B 5/066* (2013.01); *A61B 5/0084* (2013.01)

(58) Field of Classification Search
CPC ....... A61B 1/043; A61B 5/066; A61B 5/0084; A61B 5/0066; A61B 5/0071;
(Continued)

(56) References Cited

U.S. PATENT DOCUMENTS 5,377,682 A * 1/1995 Ueno ..................... A61B 8/445
600/585
6,004,271 A * 12/1999 Moore ................. A61B 8/4209
600/463
(Continued)

FOREIGN PATENT DOCUMENTS

CN 101032388 A * 9/2007
DE 102010063412 A1 * 6/2012 ......... G01B 9/02091

*Primary Examiner* — Michelle M Iacoletti
*Assistant Examiner* — Jarreas Underwood
(74) *Attorney, Agent, or Firm* — Park, Vaughan, Fleming & Dowler LLP

(57) ABSTRACT

The system includes a catheter with an internal optical fiber that carries an optical beam and an optical element, which reflects the optical beam substantially orthogonal to a rotational axis of the catheter and is coupled to the end of the optical fiber. A motor drive unit (MDU) is coupled to the catheter, wherein the MDU comprises: a rotary collimator: a catheter interface, which couples the optical fiber to the rotary collimator; and a drive motor, which rotates the rotary collimator. The MDU also includes a first dichroic mirror that combines optical paths for a fluorescence-lifetime imaging (FLIm) system and an optical coherence tomography system into a single optical path, which is coupled to the optical fiber through the rotary collimator and the catheter interface. The MDU additionally includes a multispectral detector for the FLIm system, which is electrically coupled to a data acquisition unit for the FLIm imaging system.

24 Claims, 6 Drawing Sheets

Related U.S. Application Data

(60) Provisional application No. 63/022,454, filed on May 9, 2020, provisional application No. 62/485,181, filed on Apr. 13, 2017.

(58) Field of Classification Search
CPC ... A61B 5/0073; A61B 3/102; A61B 5/14556; A61B 6/037; A61B 2090/3735; A61B 6/487; G01J 3/4406; G01B 9/02091; G01N 21/474; G01N 21/645; G01N 21/6408; G01N 21/64; G01N 2021/1787; G01N 21/255; G02B 27/30; G02B 21/0048; G02B 21/0076; G02B 21/16; G02B 27/283; G02B 27/017

See application file for complete search history.

(56) References Cited

U.S. PATENT DOCUMENTS

| | | | |
|---|---|---|---|
| 2001/0055462 A1 | 12/2001 | Seibel | |
| 2007/0291226 A1* | 12/2007 | Fujii | A61B 3/1233 |
| | | | 351/210 |
| 2009/0262361 A1* | 10/2009 | Tanioka | G01N 21/4795 |
| | | | 356/479 |
| 2011/0261367 A1* | 10/2011 | Gmitro | G01N 21/6458 |
| | | | 356/479 |
| 2012/0075639 A1* | 3/2012 | Brennan | A61B 5/0066 |
| | | | 356/479 |
| 2016/0007854 A1* | 1/2016 | Iftimia | A61B 5/065 |
| | | | 600/424 |
| 2017/0085762 A1* | 3/2017 | Obara | A61B 1/0005 |
| 2018/0310826 A1 | 11/2018 | Yoo et al. | |
| 2019/0072713 A1* | 3/2019 | Yoo | G02B 6/266 |
| 2019/0099079 A1 | 4/2019 | Yamada et al. | |
| 2019/0313941 A1 | 10/2019 | Radjabi | |
| 2019/0374195 A1 | 12/2019 | Marcu et al. | |
| 2020/0305718 A1* | 10/2020 | Ahmed | G02B 6/3624 |
| 2022/0031145 A1* | 2/2022 | Takahashi | A61B 1/00177 |

* cited by examiner

CATHETER MOTOR DRIVE UNIT THAT FACILITATES COMBINED OPTICAL COHERENCE TOMOGRAPHY AND FLUORESCENCE-LIFETIME IMAGING

RELATED APPLICATIONS

This application claims priority under 35 U.S.C. § 119 to U.S. Provisional Application No. 63/022,454, entitled "Motor Drive Unit for Intraluminal Combined Optical Coherence Tomography and Fluorescence Lifetime Imaging with Integrated Fluorescence Detection" by inventors Julien Bec and Laura Marcu, filed on 9 May 2020. This application is also a continuation-in-part of, and hereby claims priority under 35 U.S.C. § 120 to, pending U.S. patent application Ser. No. 16/500,374, entitled "Fiber-Based Multimodal Biophotonic Imaging and Spectroscopy System," by inventors Benjamin E. Sherlock, Diego R. Yankelevich, Julien Bec and Laura Marcu, filed 2 Oct. 2019. U.S. patent application Ser. No. 16/500,374 claims priority under 35 U.S.C. § 371 to PCT Application No. PCT/US2018/027372 entitled "Fiber-Based Multimodal Biophotonic Imaging and Spectroscopy System," by inventors Benjamin E. Sherlock, et al., filed on 12 Apr. 2018. PCT Application No. PCT/US2018/027372 claims priority under 35 U.S.C. § 119(e) to U.S. Provisional Application Ser. No. 62/485,181, filed on 13 Apr. 2017. The contents of the above-listed applications are incorporated by reference herein.

GOVERNMENT LICENSE RIGHTS

This invention was made with U.S. government support under grant numbers R01-HL121068 and R03-EB025565 awarded by the National Institutes of Health (NIH). The U.S. government has certain rights in the invention.

BACKGROUND

Field

The disclosed embodiments relate to techniques for characterizing biological materials by analyzing laser-induced light emissions. More specifically, the disclosed embodiments relate to a multimodal intraluminal imaging system, which provides both optical coherence tomography (OCT) imaging and fluorescence-lifetime imaging (FLIm) modalities through a single double-clad optical fiber.

Related Art

Optical imaging techniques are widely used in various medical applications to analyze tissue structure and to characterize the biochemical composition of tissues. However, the complexity of the optical tissue response makes it challenging for a single imaging modality to accurately characterize tissue structure and function. Multimodal imaging platforms, which combine two or more modalities in a single apparatus, aim to combine the strengths of complementary imaging techniques to sample a larger cross-section of the optical tissue response. Fluorescence-lifetime imaging (FLIm) and optical coherence tomography (OCT) are two such complementary imaging modalities. FLIm is a functional imaging technique, which uses the temporal dynamics of fluorescence emissions to delineate regions of biochemical contrast on a sample. (See Chang, CW; Sud. D: Mycck, MA (2007). "Fluorescence lifetime imaging microscopy." *Methods in cell biology.* 81:495-524.) In contrast, OCT uses phase-sensitive measurements of ballistically scattered photons to acquire depth resolved images of sample microstructure. (Scc Huang, D; Swanson, EA; Lin, CP; Schuman, J S; Stinson, WG; Chang, W; Hec, MR; Flotte, T; et al. (1991). "Optical Coherence Tomography." Science. 254 (5035): 1178-81.) The benefits of combining FLIm and OCT in a single system have been explored by several research groups, who implemented multimodal imaging platforms that were based around a conventional microscope frame. Although these pioneering efforts were successful, the use of bulky free-space optics prevented their use in applications where the imaging geometry is highly restricted, such as in an intraluminal environment; for example, within a blood vessel, or within a gastrointestinal tract.

Optical fibers are widely used in biophotonics applications to provide a narrow and flexible interface between a limited-access region of a sample and the imaging apparatus. However, it is impractical to use separate fibers for the two different imaging modalities because of problems related to interface flexibility, and challenges in combining and registering the signals obtained by different channels from the probe. It is also difficult to channel both short-wavelength ultraviolet FLIm signals and longer-wavelength OCT signals through the same optical fiber.

Hence, what is needed is an optical imaging system, which combines both FLIm and OCT imaging modalities in a system that operates through a single optical fiber.

SUMMARY

The disclosed embodiments relate to a multimodal intraluminal imaging system, which incorporates both an optical coherence tomography (OCT) system and a fluorescence-lifetime imaging (FLIm) system. The system includes a catheter with an internal optical fiber that carries an optical beam and an optical element, which is coupled to a distal end of the optical fiber and reflects the optical beam substantially orthogonal to the rotational axis of the catheter. The multimodal system also includes a motor drive unit (MDU) coupled to a proximal end of the catheter, wherein the MDU comprises a rotary collimator and a catheter interface, which couples the optical fiber in the catheter to the rotary collimator, and a drive motor, which applies a rotary motion to the rotary collimator. The MDU also includes a first dichroic mirror that combines optical paths for the FLIm imaging system and the OCT imaging system into a single optical path, which is coupled to the optical fiber in the catheter through the rotary collimator and the catheter interface. The MDU additionally includes a multispectral detector for the FLIm imaging system, which is electrically coupled to a data acquisition unit for the FLIm imaging system, which is located externally to the MDU.

In some embodiments, the rotary collimator includes an air bearing.

In some embodiments, the drive motor is indirectly coupled to the rotary collimator, and a main shaft of the rotary collimator includes an optical encoder, which is coupled to a closed-loop control system that controls a rotational speed of the rotary collimator by actively controlling the drive motor.

In some embodiments, the drive motor is indirectly coupled to the rotary collimator through a belt or a gear train.

In some embodiments, the multispectral detector for the FLIm imaging system comprises: a second dichroic mirror configured to separate FLIm excitation and collection signals; one or more additional dichroic mirrors configured to separate the FLIm collection signal into distinct spectral bands; two or more solid state detectors configured to detect the separated spectral bands; and electrical outputs for communicating FLIm signals from the two or more solid state detectors to the data acquisition unit for the FLIm system.

In some embodiments, the optical fiber comprises a double-clad optical fiber, which transmits both UV light and coherent infrared light through two concentric light-guiding regions, thereby facilitating generation of precisely co-registered optical data for the FLIm imaging system and the OCT imaging system.

In some embodiments, the MDU further includes a FLIm collimator, which is configured to generate a collimated beam from UV light received through a fiber optic link from a FLIm excitation laser, which is part of the FLIm imaging system.

In some embodiments, the MDU further includes a FLIm excitation laser, which is configured to generate a collimated UV light beam.

In some embodiments, the MDU further includes an OCT collimator, which is configured to generate a collimated beam from light received through an optical fiber from the OCT imaging system, which is located outside of the MDU.

In some embodiments, the OCT imaging system includes an infrared light source and an interferometer with a reference arm and a sample arm.

In some embodiments, the OCT imaging system makes use of a polarization sensitive optical coherence tomography (PS-OCT) imaging technique.

In some embodiments, the optical element comprises a curved mirror that reflects and focuses light from the optical fiber in a direction substantially orthogonal to the rotational axis of the catheter.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Multimodal Imaging System

Figure 1:
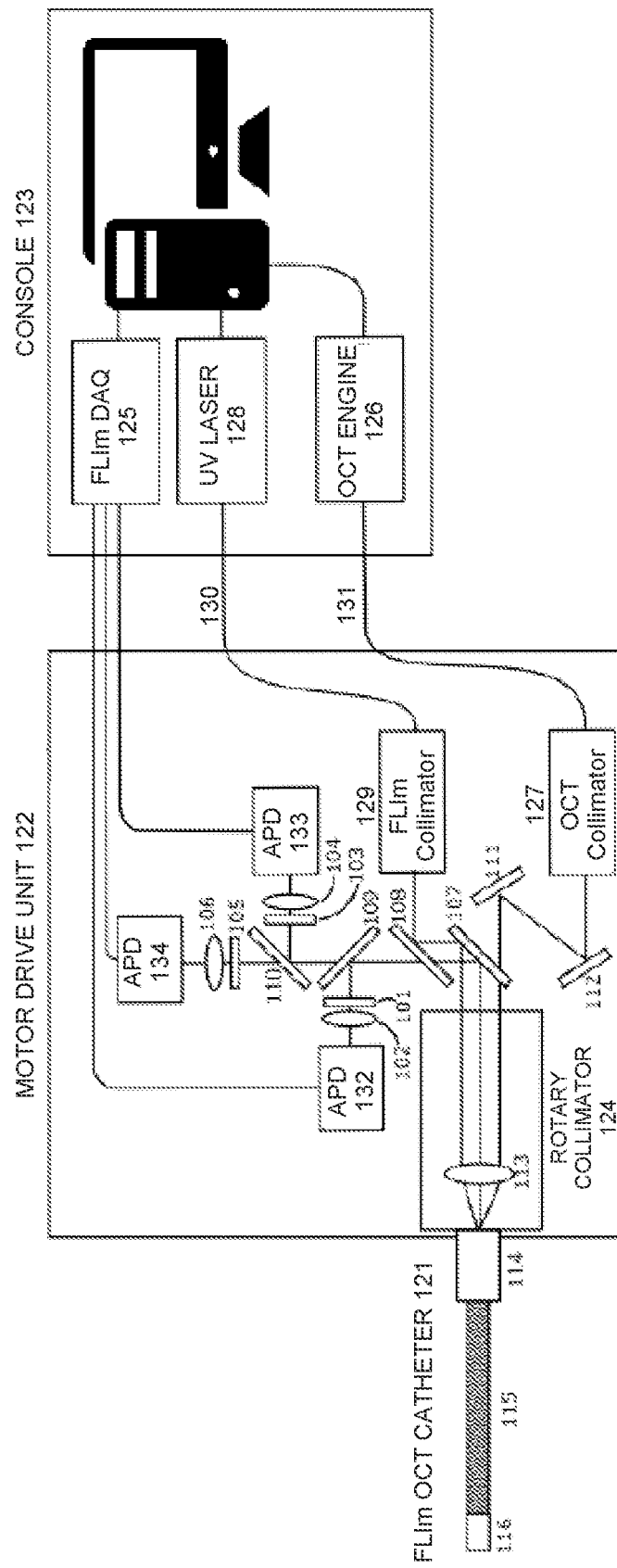
FIG. 1 presents a diagram of a multimodal intraluminal imaging system that facilitates simultaneous FLIm imaging and OCT imaging in accordance with the disclosed embodiments.

FIG. 1 presents a diagram of a multimodal intraluminal imaging system 100 that facilitates simultaneous FLIm imaging and OCT imaging in accordance with the disclosed embodiments. As illustrated in FIG. 1, this multimodal intraluminal imaging system 100 includes a FLIm OCT catheter 121, which is coupled to a motor drive unit (MDU) 122, and a console 123.

FLIm OCT catheter 121 comprises a catheter shaft 115 with an internal optical fiber that carries an optical beam. An optical element 116 is coupled to a distal end of the catheter shaft and reflects the optical beam substantially orthogonal to the rotational axis of the catheter. (The structure of this optical element 116 is described in more detail below with reference to FIG. 6.) A proximal end of catheter shaft 115 is coupled to a catheter interface 114, which couples the optical fiber in the catheter shaft 115 to a rotary collimator 124 within MDU 122.

MDU 122 also includes a drive motor (not shown in FIG. 1), which applies a rotary motion to rotary collimator 124. MDU 122 additionally includes the previously mentioned rotary collimator 124 with a lens 113, which collimates light that is directed to the optical fiber in catheter shaft 115.

MDU 122 also includes a dichroic mirror 107, which combines optical paths for the FLIm imaging system and the OCT imaging system into a single optical path, which is coupled to the optical fiber in catheter shaft 115 through the rotary collimator 124 and the catheter interface 114.

The OCT imaging system includes an OCT engine 126 within console 123, which includes an infrared light source (not shown); and an interferometer with a reference arm and a sample arm (not shown). (For more details about OCT engine 126, please see Huang, D; Swanson, EA; Lin, CP; Schuman, J S; Stinson, WG; Chang, W; Hec, M R; Flotte, T; et al. (1991). "Optical Coherence Tomography." Science. 254 (5035): 1178-81.) OCT engine 126 is coupled to an OCT collimator 127 within MDU 122 through an optical fiber 131. OCT collimator 127 is configured to generate a collimated beam that passes through infrared (IR) beam adjustment mirrors 111-112, which direct the collimated beam through dichroic mirror 107 into rotary collimator 124.

The FLIm imaging system includes a UV laser 128 within console 123, which directs a UV excitation beam through an optical fiber 130 into a FLIm collimator 129. FLIm collimator 129 is configured to generate a collimated beam of UV light that feeds into a dichroic mirror 108, which separates FLIm excitation and collection signals. The FLIm excitation signal then feeds through dichroic mirror 107 into rotary collimator 124, and the FLIm collection signal feeds into a set of components within MDU 122, which comprise a "multispectral detector" for the FLIm imaging system. This multispectral detector is electrically coupled to a data acquisition unit (DAQ) 125 for the FLIm imaging system located in console 123.

As illustrated in FIG. 1, the multispectral detector within MDU 122 includes dichroic mirrors 109 and 110, which are configured to separate the FLIm collection signal into three distinct spectral bands, namely a first spectral band, a second spectral band and a third spectral band. The first spectral band feeds through filter 101 and lens 102 into avalanche photodetector (APD) 132, which converts the first spectral band into an electrical signal that feeds into FLIm DAQ 125 within console 123. The second spectral band feeds through filter 103 and lens 104 into APD 133, which converts the second spectral band into an electrical signal that also feeds into FLIm DAQ 125. The third spectral band feeds through filter 105 and lens 106 into APD 134, which converts the third spectral band into an electrical signal that similarly feeds into FLIm DAQ 125.

Figure 2:
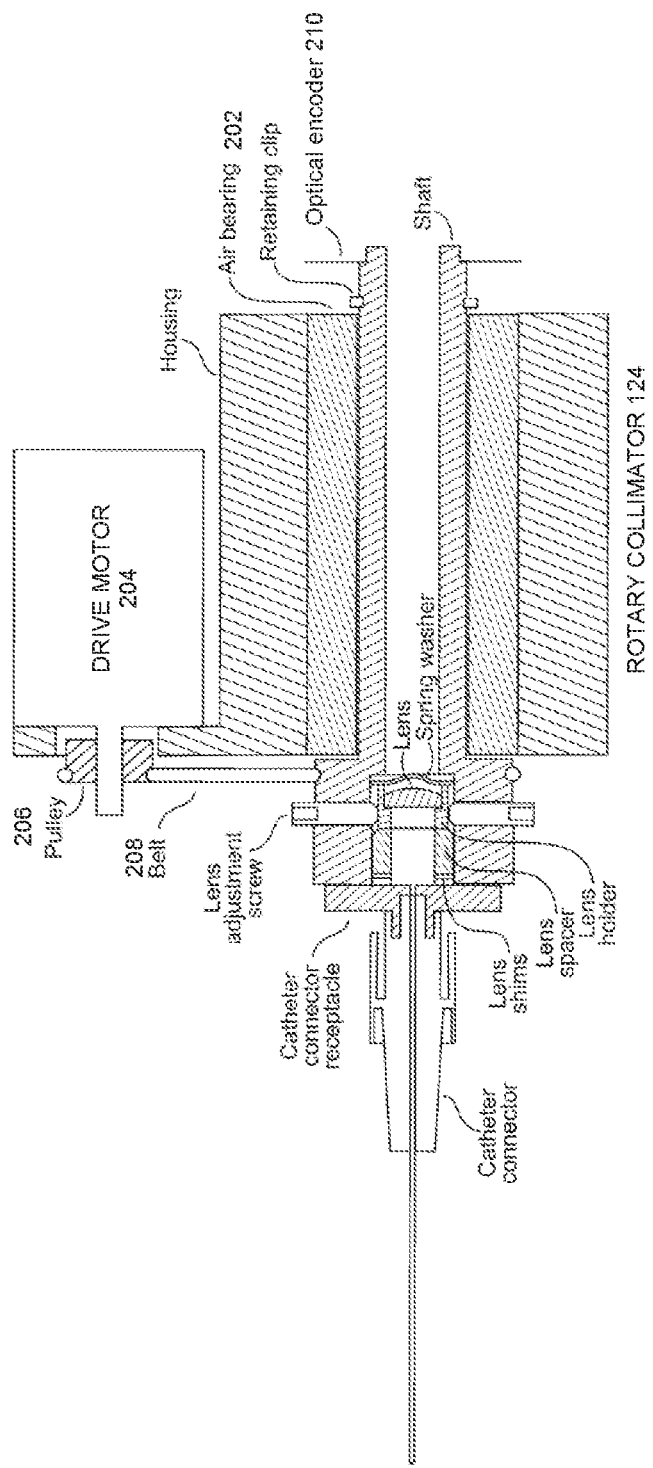
FIG. 2 illustrates details of the rotary collimator assembly, which makes use of an air bearing, in accordance with the disclosed embodiments.

FIG. 2 illustrates details of the rotary collimator 124, which includes an air bearing 202, in accordance with the disclosed embodiments. Note that air bearing 202 uses a thin film of gas to provide a low friction, load-bearing interface between surfaces and provides the following advantages over mechanical bearings: (1) an air bearing makes it possible to attain more precise positioning than a normal mechanical bearing; and (2) a normal mechanical bearing has a higher run-out error that leads to misalignment/positioning errors resulting in optical beam eccentricity, which is not cyclic with the angular position of the bearing. Adjusting the position of the collimator lens can only address beam eccentricity variations that are synchronous with the collimator rotation, and therefore may not be sufficient to correct the effect of bearing runout. In contrast, mechanical inaccuracies in an air bearing generate a run-out error that is correlated with the rotational speed of the bearing, which can be efficiently reduced by adjusting the position of the collimator lens.

Figure 3:
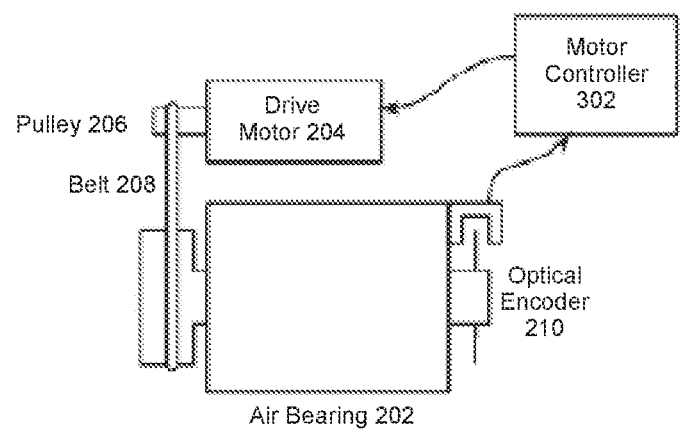
FIG. 3 illustrates details of a closed-loop speed control system for the rotary collimator in accordance with the disclosed embodiments.

Drive motor 204 is indirectly coupled to rotary collimator 124 through a pulley 206 and a belt 208. Note there presently do not exist drive motors that are built into an air bearing, so it is necessary to use a drive motor that is located off to the side of the air bearing, and is indirectly coupled to the air bearing using a belt 208. Unfortunately, belts can suffer from vibration issues and slippage, which can give rise to errors in rotational position that limit the accuracy of associated imaging operations. To remedy this problem, the main shaft of rotary collimator 124 includes an optical encoder 210, which is coupled to a closed-loop control system that controls a rotational speed of the rotary collimator by using a motor controller 302 to actively control drive motor 204 as is illustrated in FIG. 3.

Double-Clad Optical Fiber

The disclosed embodiments use a single optical fiber interface to perform simultaneous FLIm and OCT operations. Note that the combination of two modalities in a single optical fiber places stringent requirements on the fiber itself. OCT requires light to be guided in a single spatial mode, whereas FLIm benefits greatly from the increased fluorescence collection cross-section given by multimode fibers. To accommodate these requirements a double-clad optical fiber is used, which combines a central single-mode core and surrounding multimode inner cladding in single, concentric fiber package.

Figure 4A:
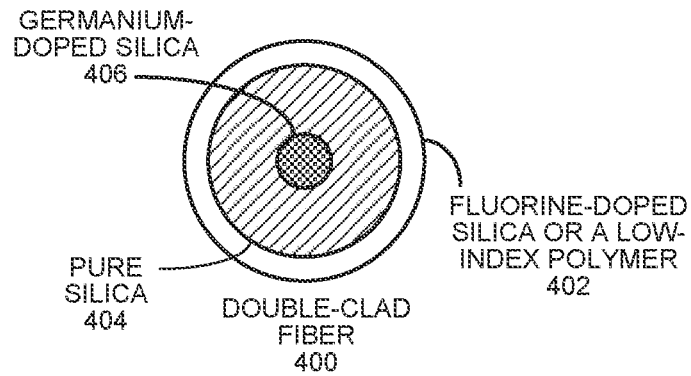
FIG. 4A illustrates a cross-sectional view of a double-clad optical fiber in accordance with the disclosed embodiments.

To meet the requirements of this multimodal imaging system, a commercially available double-clad fiber (DCF) can be used. In the embodiment illustrated in FIG. 4A, the DCF 400 comprises a high-index, Germanium-doped silica central core 406 and a pure silica multimode inner cladding 404 with diameters of 9 μm and 105 μm, respectively. The inner cladding 404 is surrounded by an outer cladding 402 composed of a low-index material, such as fluorine-doped silica or a low index-polymer, so the resulting outer diameter of the fiber is 125 μm. The core and inner cladding numerical apertures (NA) are 0.12 and 0.2, respectively.

Figure 4B:
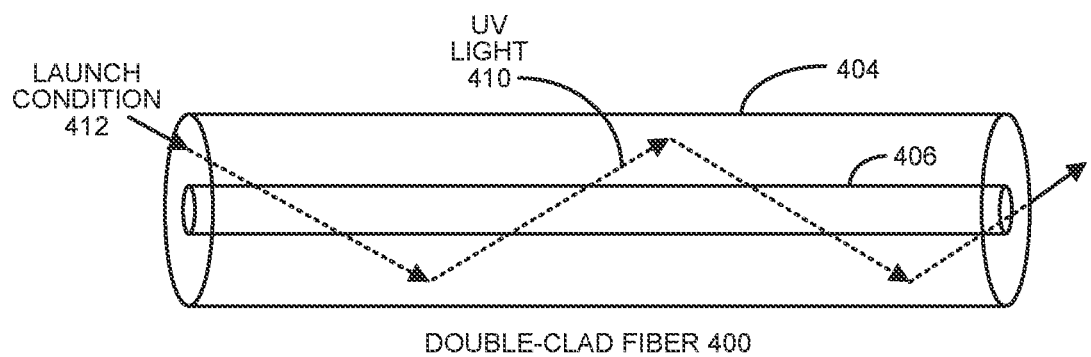
FIG. 4B illustrates light circulating through a silica inner cladding around a high-index Germanium-doped silica optical core in accordance with the disclosed embodiments.

Referring to FIG. 4B, in order to minimize interactions between UV light 410 travelling through inner cladding 404 and central core 406, UV light 410 is directed into inner cladding 404 with a launch condition 412 that ensures that the UV light 410 circulates around central core 406 instead of impacting central core 406. This minimizes interactions with central core 406, thereby minimizing associated transmission losses.

Figure 5:
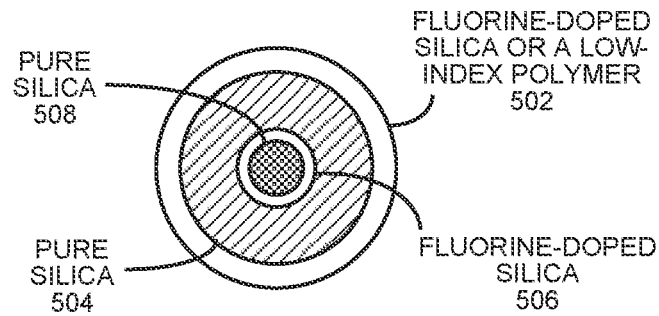
FIG. 5 illustrates a cross-sectional view of another double-clad optical fiber, which surrounds the pure silica optical core with fluorine-doped silica in accordance with the disclosed embodiments.

In the alternative embodiment illustrated in FIG. 5, the DCF comprises a pure silica single-mode central core 508 surrounded by a ring of low-index Fluorine-doped silica 506. The central core 508 and surrounding ring 506 are enclosed by a pure silica inner cladding 504, which is itself enclosed by an outer cladding 502, which is composed of a low-index material, such as fluorine-doped silica or a low-index polymer. In this embodiment, the surrounding ring of doped silica 506 eliminates interference between light propagating in the central core 508 and the inner cladding. Hence, in this embodiment, it is not necessary to guide the light in the inner cladding 504 to circulate around central core 508 to minimize unwanted interactions that lead to transmission losses.

Optical Element

Figure 6:
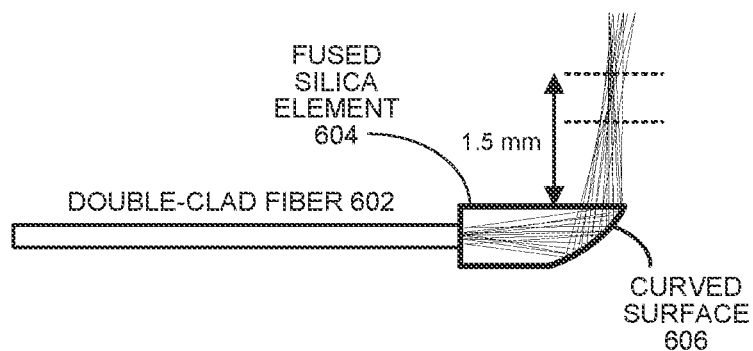
FIG. 6 illustrates a reflective micro optic that facilitates both beam focusing and reflection in accordance with the disclosed embodiments.

FIG. 6 illustrates an optical element, which is used to perform the imaging operation. The optical element comprises a fused silica element 604, which is terminated by a curved surface 606 with a reflective coating that performs both beam focusing and reflection operations for an optical beam that originates from a double-clad fiber 602. This design is inherently broadband because the optical beam is transmitted through pure glass and reflections are not subject to chromatic aberrations. An important aspect of the performance of the proposed solution is to be able to fully specify the geometry of the reflective optical surface. This is because different radii of curvature are required to achieve an identical focal plane in the axial and transaxial directions at a target location, and astigmatisms introduced by other elements in the beam path such as the device's sheath need to be corrected.

Alternatively, the optical element can comprise a standard ball lens obtained from a fused and angle-polished no core fiber section spliced to the DCF fiber, which can be used to reflect and focus the light substantially orthogonal to the rotational axis as described in [Shishkov, M., Tearney, G. J. & Bouma, B. E. Scultpured optical fiber tips for narrow diameter optical catheters. SE5 (2014). doi: 10.1364/bio.2004.se5]

Process of Operating a Multimodal Imaging System

Figure 7:
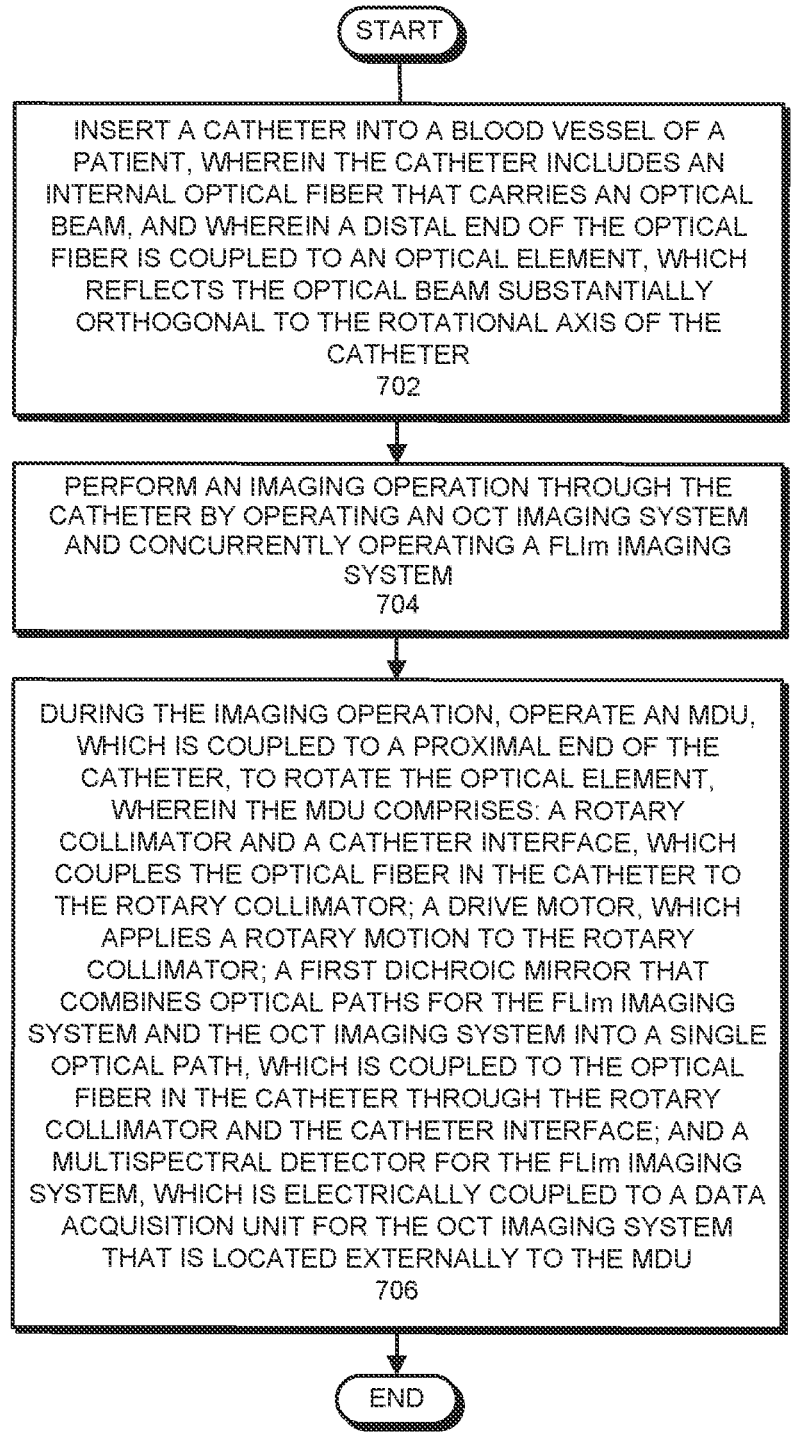
FIG. 7 presents a flow chart illustrating a process for operating a multimodal imaging system in accordance with the disclosed embodiments.

FIG. 7 presents a flow chart illustrating a process for performing a multimodal intraluminal imaging operation in accordance with the disclosed embodiments. During this process, a catheter is first inserted into a blood vessel of a patient, wherein the catheter includes an internal optical fiber that carries an optical beam, and wherein a distal end of the optical fiber is coupled to an optical element, which reflects the optical beam substantially orthogonal to the rotational axis of the catheter (step 702). Next, the system performs an imaging operation through the catheter by operating an optical coherence tomography (OCT) imaging system, and concurrently operating a fluorescence-lifetime imaging (FLIm) imaging system (step 704). During this imaging operation, the system operates a motor drive unit (MDU), which is coupled to a proximal end of the catheter, to rotate the optical element, wherein the MDU comprises: a rotary collimator and a catheter interface, which couples the optical fiber in the catheter to the rotary collimator; a drive motor, which applies a rotary motion to the rotary collimator; a first dichroic mirror that combines optical paths for the FLIm imaging system and the OCT imaging system into a single optical path, which is coupled to the optical fiber in the catheter through the rotary collimator and the catheter interface; and a multispectral detector for the FLIm imaging system, which is electrically coupled to a data acquisition unit for the OCT imaging system that is located externally to the MDU (step 706).

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A multimodal intraluminal imaging system, comprising:
   an optical coherence tomography (OCT) system;
   a fluorescence-lifetime imaging (FLIm) system;
   a catheter with an internal optical fiber that carries an optical beam, wherein the optical fiber comprises a double-clad optical fiber that transmits both UV light and coherent infrared light through two concentric light-guiding regions, thereby facilitating generation of precisely co-registered optical data for the FLIm system and the OCT system;
   an optical element coupled to a distal end of the internal optical fiber, wherein the optical element reflects the optical beam orthogonal to a rotational axis of the catheter; and
   a motor drive unit (MDU) coupled to a proximal end of the internal optical fiber, wherein the MDU comprises:
      a rotary collimator,
      a catheter interface that couples the internal optical fiber of the catheter to the rotary collimator,
      a drive motor that applies a rotary motion to the rotary collimator,
      a first dichroic mirror that combines optical paths for the FLIm system and the OCT system into a single optical path, which is coupled to the internal optical fiber in the catheter through the rotary collimator and the catheter interface, and
      a multispectral detector for the FLIm system that is electrically coupled to a data acquisition unit for the FLIm system that is located externally to the MDU.

2. The multimodal imaging system of claim 1, wherein the rotary collimator includes an air bearing.

3. The multimodal imaging system of claim 2, wherein:
   the drive motor is indirectly coupled to the rotary collimator; and
   a main shaft of the rotary collimator includes an optical encoder, which is coupled to a closed-loop control system that controls a rotational speed of the rotary collimator by actively controlling the drive motor.

4. The multimodal imaging system of claim 3, wherein the drive motor is indirectly coupled to the rotary collimator through one of:
   a belt; and
   a gear train.

5. The multimodal imaging system of claim 1, wherein the multispectral detector for the FLIm system comprises:
   a second dichroic mirror configured to separate FLIm excitation and collection signals;
   one or more additional dichroic mirrors configured to separate the FLIm collection signal into distinct spectral bands;
   two or more solid state detectors configured to detect the separated spectral bands; and
   electrical outputs for communicating FLIm signals from the two or more solid state detectors to the data acquisition unit for the FLIm system.

6. The multimodal imaging system of claim 1, wherein the double-clad optical fiber comprises:
   a single-mode central core composed of pure silica surrounded by a ring of low-index doped silica;
   a multimode inner cladding composed of pure silica surrounding the single-mode central core; and
   an outer cladding surrounding the inner cladding that is composed of a low-index material comprising doped silica or a low-index polymer.

7. The multimodal imaging system of claim 1, wherein the MDU further includes a FLIm collimator, which is configured to generate a collimated beam from UV light received through a fiber optic from a FLIm excitation laser, which is part of the FLIm system.

8. The multimodal imaging system of claim 1, wherein the MDU further includes a FLIm excitation laser, which is configured to generate a collimated UV light beam.

9. The multimodal imaging system of claim 8, wherein the OCT system comprises:
   an infrared light source; and
   an interferometer with a reference arm and a sample arm.

10. The multimodal imaging system of claim 1, wherein the MDU further includes an OCT collimator, which is configured to generate a collimated beam from light received through an optical fiber from the OCT system, which is located outside of the MDU.

11. The multimodal imaging system of claim 1, wherein the optical element attached to the distal end of the catheter comprises a curved mirror that reflects and focuses light from the optical fiber in a direction orthogonal to the rotational axis of the catheter.

12. A method for performing multimodal intraluminal imaging, the method comprising:
providing a catheter that is inserted into a blood vessel of a patient, wherein:
the catheter includes an internal optical fiber that carries an optical beam;
a distal end of the optical fiber is coupled to an optical element that reflects the optical beam orthogonal to a rotational axis of the catheter; and
the optical fiber comprises a double-clad optical fiber that transmits both UV light and coherent infrared light through two concentric light-guiding regions, thereby facilitating generation of precisely co-registered optical data for the FLIm system and the OCT system; and
performing an imaging operation through the catheter by:
operating an optical coherence tomography (OCT) system;
concurrently operating a fluorescence-lifetime imaging (FLIm) system; and
during the concurrent operation of the OCT system and the FLIm system, operating a motor drive unit (MDU), which is coupled to a proximal end of the catheter, to rotate the optical element during the imaging operation, wherein the MDU comprises:
a rotary collimator and a catheter interface that couples the optical fiber in the catheter to the rotary collimator;
a drive motor that applies a rotary motion to the rotary collimator;
a first dichroic mirror that combines optical paths for the FLIm system and the OCT system into a single optical path, which is coupled to the optical fiber in the catheter through the rotary collimator and the catheter interface; and
a multispectral detector for the FLIm system that is electrically coupled to a data acquisition unit for the FLIm system that is located externally to the MDU.

13. The method of claim 12, wherein the rotary collimator includes an air bearing.

14. The method of claim 13, wherein:
the drive motor is indirectly coupled to rotary collimator; and
a main shaft of the rotary collimator includes an optical encoder, which is coupled to a closed-loop control system that controls a rotational speed of the rotary collimator by actively controlling the drive motor.

15. A multimodal intraluminal imaging system, comprising:
an optical coherence tomography (OCT) system;
a fluorescence-lifetime imaging (FLIm) system;
a catheter with an internal optical fiber that carries an optical beam, wherein the optical fiber comprises a double-clad optical fiber that transmits both UV light and coherent infrared light through two concentric light-guiding regions, thereby facilitating generation of precisely co-registered optical data for the FLIm system and the OCT system;
an optical element coupled to a distal end of the optical fiber, wherein the optical element reflects the optical beam orthogonal to a rotational axis of the catheter;
a motor drive unit (MDU) coupled to a proximal end of the catheter, wherein the MDU comprises:
a rotary collimator that includes an air bearing;
a catheter interface that couples the optical fiber in the catheter to the rotary collimator; and
a drive motor that applies a rotary motion to the rotary collimator; and
a first dichroic mirror that combines optical paths for the FLIm system and the OCT system into a single optical path, which is coupled to the optical fiber in the catheter through the rotary collimator and the catheter interface.

16. The multimodal imaging system of claim 15, wherein the drive motor is indirectly coupled to the rotary collimator; and
wherein a main shaft of the rotary collimator includes an optical encoder, which is coupled to a closed-loop control system that controls a rotational speed of the rotary collimator by actively controlling the drive motor.

17. The multimodal imaging system of claim 16, wherein the drive motor is indirectly coupled to the rotary collimator through one of:
a belt; and
a gear train.

18. The multimodal imaging system of claim 15, wherein the FLIm system comprises:
a second dichroic mirror configured to separate FLIm excitation and collection signals;
one or more additional dichroic mirrors configured to separate the FLIm collection signal into distinct spectral bands;
two or more solid state detectors configured to detect the separated spectral bands; and
electrical outputs for communicating FLIm signals from the two or more solid state detectors to a data acquisition unit for the FLIm system.

19. The multimodal imaging system of claim 15, wherein the double-clad optical fiber comprises:
a single-mode central core composed of pure silica surrounded by a ring of low-index doped silica;
a multimode inner cladding composed of pure silica surrounding the single-mode central core; and
an outer cladding surrounding the inner cladding that is composed of a low-index material comprising doped silica or a low-index polymer.

20. The multimodal imaging system of claim 15, wherein the FLIm system includes a FLIm collimator, which is configured to generate a collimated beam from UV light received through a fiber optic from a FLIm excitation laser.

21. The multimodal imaging system of claim 15, wherein the FLIm system includes a FLIm excitation laser, which is configured to generate a collimated UV light beam.

22. The multimodal imaging system of claim 15, wherein the OCT system includes an OCT collimator, which is configured to generate a collimated beam from light received through an optical fiber from the OCT system.

23. The multimodal imaging system of claim 22, wherein the OCT system additionally comprises:
an infrared light source; and
an interferometer with a reference arm and a sample arm.

24. The multimodal imaging system of claim 15, wherein the optical element attached to the distal end of the catheter comprises a curved mirror that reflects and focuses light from the optical fiber in a direction orthogonal to the rotational axis of the catheter.

* * * * *